United States Patent [19]
Günther

[11] Patent Number: 5,005,576
[45] Date of Patent: Apr. 9, 1991

[54] OPTICAL PROBE

[75] Inventor: Martin Günther, Wildberg, Fed. Rep. of Germany

[73] Assignee: Hewlett-Packard Company, Palo Alto, Calif.

[21] Appl. No.: 332,080

[22] Filed: Mar. 30, 1989

[30] Foreign Application Priority Data

Apr. 9, 1988 [EP] European Pat. Off. ........ 88105676.6

[51] Int. Cl.$^5$ .............................................. A61B 6/00
[52] U.S. Cl. .................................... 128/634; 128/665
[58] Field of Search ................ 128/633, 634, 665, 635

[56] References Cited

U.S. PATENT DOCUMENTS

| | | | |
|---|---|---|---|
| 3,674,013 | 7/1972 | Polanni | 128/634 |
| 4,557,900 | 12/1985 | Heitzman | 128/634 |
| 4,568,444 | 2/1986 | Nakamura et al. | 128/635 |

OTHER PUBLICATIONS

IEEE Transactions on Biomedical Engineering, vol. BME-33, No. 2, Feb. 1986.

*Primary Examiner*—Kyle L. Howell
*Assistant Examiner*—John C. Hanley

[57] ABSTRACT

Optical probes for the invasive measurement of blood parameters consist of at last one sensor, each of these sensors having a diffusion zone with a selective membrane. The sensor or the sensors are surrounded by a stabilizing sheath. This sheath is to be fastened on sensor(s) by a glue. A silicone glue provides the feature that gas molecules can diffuse through it; therefore, blood gas sensors such as $pO_2$ sensors or $pCO_2$ sensors may be completely embedded in said glue. If a pH sensor is used, it must be placed in the top position of the horizontally lying sheath during manufacturing. The silicone glue then does not cover the diffusion zone of the pH sensor completely. Further, silicone glue provides additional elasticity which improves sensor characteristics.

3 Claims, 3 Drawing Sheets

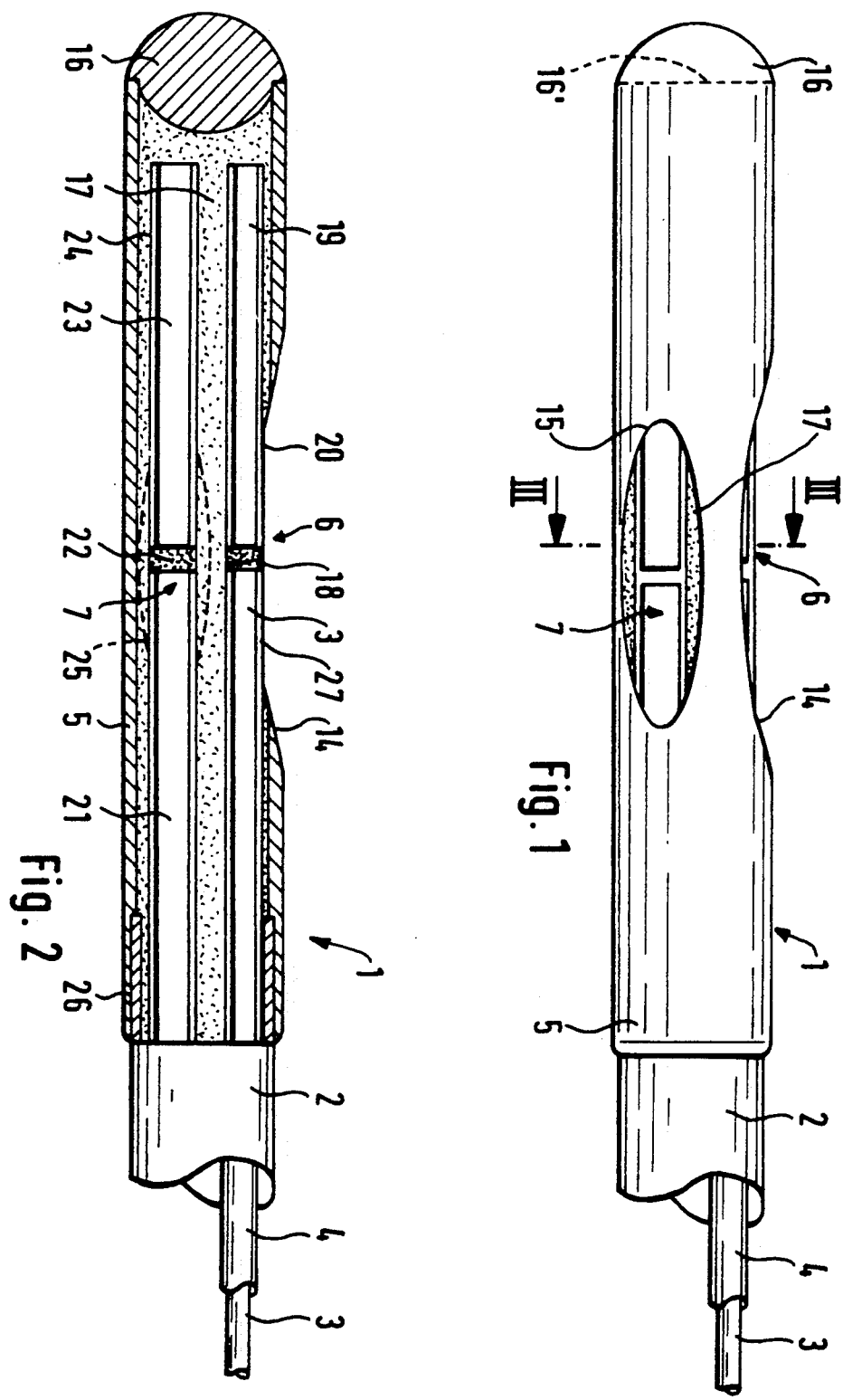

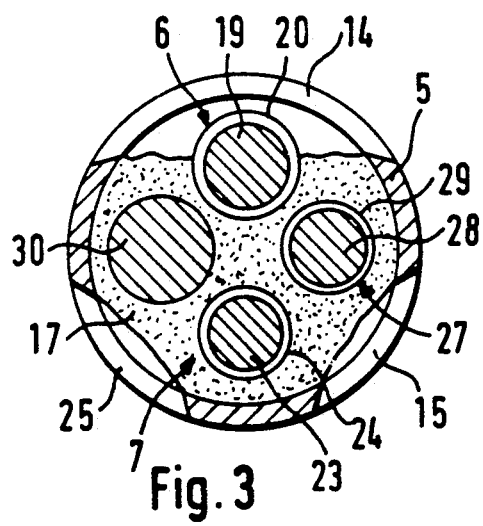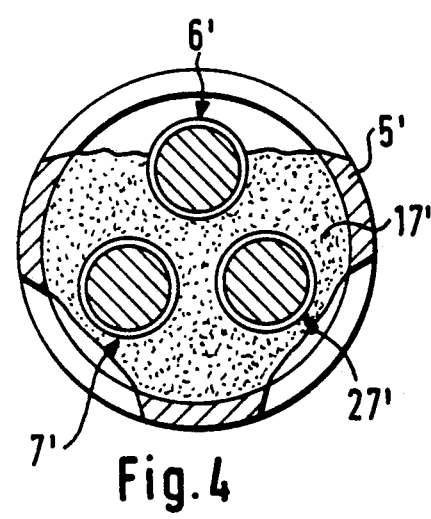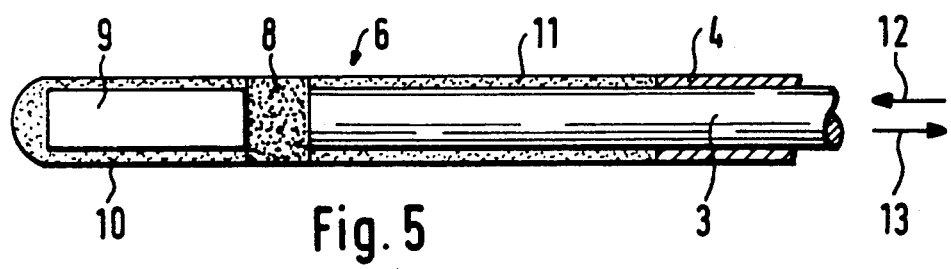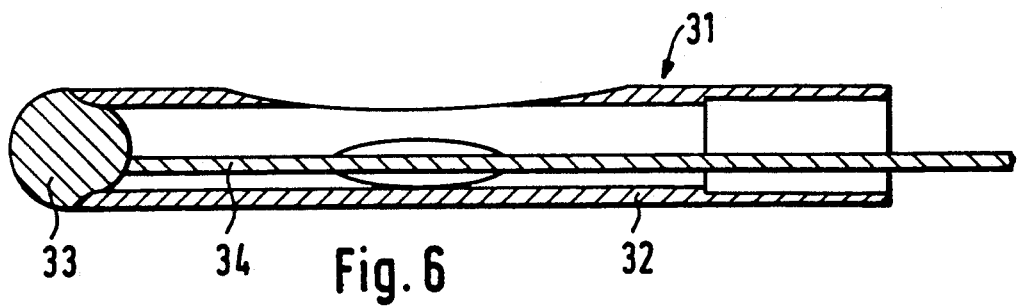

OPTICAL PROBE

BACKGROUND OF THE INVENTION

This invention relates to a method for manufacturing an optical probe for the invasive measurement of blood parameters, said optical probe comprising at least one sensor sensitive to a blood gas parameter such as $pO_2$ or $pCO_2$ and at least one additional sensor sensitive to the pH value of the blood, said sensors having selective membranes, and said optical probe further comprising a sheath at least partially covering said sensors and fastened on said sensor by a glue.

Probes for the invasive measurement of blood parameters consist of at least one sensor comprising an optical fiber, said fiber ending up with a gel zone containing a dye. The optical density or another optical parameter of said dye varies with the blood parameter (such as pH) to be measured. On the other side of the dye-containing gel, a reflector is positioned. The end of the fiber, the gel and the reflector are surrounded by a semi-permeable envelope (for example, a hydrogen ion permeable envelope in the case of a pH sensor) to keep the gel in place.

Light from this optical fiber passes the dye-containing gel, is reflected by said reflector, passes the gel again and is transmitted through the optical fiber to an appropriate detector which measures light attenuation or changes in other optical parameters caused by the dye. This attenuation or change is a function of the blood parameter to be measured and the relation between attenuation, absorbance or the change of another optical parameter and the blood parameter is well-known.

Such a probe can be introduced into a patient's artery to measure—depending on the dye—various blood parameters such as pH, $pO_2$ or $pCO_2$.

For a more detailed description of fiber optic pH measurement, reference is made to "A Miniature Fiber Optic pH Sensor for Physiological Use", Journal of Biomechanical Engineering, May 1980, pg. 141 ff.

It is a major goal of probe development to combine more than one sensor in a single probe. The reason is that a patient should not be overstrained with various probes introduced in his arteries. Such a combination or multiple sensor probe may, for example, contain a pH sensor, a $pO_2$ sensor, a $pCO_2$ sensor and/or a stabilizing element such as a wire.

In the case of a multiple sensor probe, the sensors have to be coupled mechanically. This can be achieved by use of a sheath covering the front end of the probe and being appropriately perforated to allow the ions (in the case of a pH sensor) or the gas molecules (in the case of $pO_2$ or a $pCO_2$ sensor) to reach the permeable envelope of the sensor, pass it and diffuse into the dye-containing gel. The sheath has to be secured by a glue or adhesive.

A serious disadvantage when manufacturing such probes is that—when the glue is applied to the sensor—the glue tends to move or creep along the same, thereby covering the diffusion zones of the selective membranes, i.e. the permeable envelopes in the region of the dye-containing gel. The result is that the ions or gas molecules cannot or can hardly reach the selective membrane. Such a probe is either insensitive or has a very long time constant in the range of half an hour or more which makes it unusable.

SUMMARY OF THE INVENTION

It is a major objective of the present invention to propose a method for manufacturing an optical probe which ensures that the ions and/or gas molecules can reach the appropriate sensors, said method also ensuring sufficient mechanical stability of the probe.

According to the present invention, this problem is solved by the following manufacturing steps:

(1) The sheath is placed in an approximately horizontal position,
(2) the sensors are introduced into the sheath such that
    (2.1) the pH sensor is in the top position, whereas
    (2.2) the blood gas sensors are placed below the pH sensor,
(3) a glue which allows diffusion of gas molecules in its hardened state is introduced into the sheath.

According to the proposed method, a glue which allows gas molecules to pass or penetrate is used to fasten the sheath on the sensors. This glue is introduced into the sheath through one of its openings or—by means of underpressure—through the tubing. In the sheath, the pH sensor is placed in the top position, whereas the other sensors are placed below the pH sensor. In this way, the glue will cover the blood gas sensors (e.g. $pO_2$ or $pCO_2$) completely, whereas the pH sensor will only be covered by the glue at its bottom side. It is an important finding of the present invention that the glue does not tend to creep on the top of the pH sensor. Therefore, the top side of the pH sensor is not covered by the glue, whereas its underside is fixed to the other sensors and to the sheath, respectively. This is an important feature as the pH sensor has to be—on one hand—fastened securely to the sheath, whereas—on the other hand—the hydrogen ions must be able to reach the permeable envelope and the diffusion zone of the pH sensor. It has been found that the glue at the underside of the pH sensor does hardly affect the response time or the sensitivity of the sensor; on the contrary, fastening the sensor at its underside as described has several advantages which will be discussed below.

Another aspect of the invention is that the glue allows gas molecules to reach the blood gas sensors, e.g. the sensors sensitive to the $pO_2$ or the $pCO_2$ value of the blood. Therefore, these sensors may be completely embedded in the glue thereby ensuring mechanical stability.

A serious problem of a $pCO_2$ sensor is that it is often not only sensitive to $CO_2$ molecules, but also cross-sensitive to hydrogen ions ("pH interference"). The present invention offers a solution for that problem in that the used glue is only permeable for gas molecules, but not for hydrogen ions Therefore, the gas molecules can reach the $pCO_2$ sensor completely embedded in the glue, but not the hydrogen ions. In this way, pH interference of the $pCO_2$ sensor can be avoided.

Usually, the sheath surrounding the sensors has openings or windows allowing the blood to find its way to the sensors. When using an ordinary glue which is not permeable for gas molecules, it must not only be ensured that this glue does not cover the outside of the sensors directed to said openings, but it has also to be ensured that the diffusion zones of the sensors are placed directly under or adjacent to said openings.

It is a major advantage of the present invention that the diffusion zones of the sensors must not be placed directly under or adjacent to the openings. Therefore, mechanical assembling of the probe is less critical. This is achieved by using a glue which allows the gas molecules to diffuse through it.

Preferably, the glue as described above is a silicone glue, e.g. RTV12 or RTV627 manufactured by General Electric (RTV=Room Temperature Vulcanization). Such a silicone glue is especially well-suited for the present application. In particular, the hardened silicone glue has elastic characteristics. This allows the sensors to move up to a certain degree when the probe is exposed to temperature changes. In particular, the probe may be sterilized at $-78°$ C., e.g. using cryogamma sterilization. This is not possible when using other glues which are less elastic than silicone glue as, in this case, there would be the danger of irreversible damage of the sensor.

Further, it has turned out that the influence of sterilization at low temperatures on sensor intensity is minimal when using a silicone glue. A comparison of the effect of cold sterilization on sensor intensity between an ordinary glue and silicone glue will be given in the detailed description.

As the positioning of the sensors within the sheath is less critical when using a silicone glue or another glue permeable for gas molecules, the openings or windows of the sheath may be better adapted to physiological requirements. In particular, cavities or projecting edges may be omitted which is important to avoid the danger of a thrombosis.

Finally, it has to be pointed out that it has been observed that the response time of the various sensors is considerably faster than in sensors manufactured according to the state of the art.

The invention further relates to an optical probe for the invasive measurement of blood parameters comprising at least one sensor sensitive to a blood gas parameter such as $pO_2$ or $pCO_2$, said sensor having a diffusion zone covered by a selective membrane, and said optical probe further comprising a sheath at least partially covering said sensor and fastened on said sensor by a glue. According to the invention, said glue is a silicone glue. Apart from the advantages of a silicone glue as outlined above, there is an additional advantage: If a probe comprising only blood gas parameter sensors (i.e. no pH sensor) is manufactured, the $pO_2$ or $pCO_2$ (or some other blood gas) sensor may be placed within the sheath in any position. Therefore, the manufacturing process becomes easier. Furthermore, the mechanical stability of the sensor is improved considerably as it may be placed centrally or near the longitudinal axis of the sheath. The amount of glue surrounding the sensor additionally provides increased elasticity, i.e. the sensor may move upon temperature changes.

In any case, the sheath provides the necessary mechanical stability for the sensor or the sensors which are rather flexible in the region of the diffusion zone; in this region, only the semipermeable envelope connects the optical fiber with the reflector. Therefore, the sensor itself is not stable enough to be introduced into a patient's artery. As the sheath is used as a stabilizing element particularly for the region of the diffusion zones, it is understood that such an optical probe may also comprise only one blood gas sensor which needs stabilizing, i.e. the invention is not restricted to optical probes comprising two or more sensors.

Such an optical probe may also comprise an additional sensor sensitive to the pH value of the blood. In this case, according to the invention, the silicone glue covers the selective membrane of the pH sensor only partially, whereas it covers the selective membrane of the blood gas sensitive sensor completely or almost completely.

The optical probe may also comprise two or more blood gas ($pO_2$, $pCO_2$) sensors and/or a wire which is connected to a metal cap fixed on the top of said sheath. Such a wire provides perfect strain relieving of the probe and ensures that the sheath cannot break off inside the artery of a patient which could cause an embolism.

In the accompanying drawings, a preferred embodiment of the present invention is shown. More features and advantages of the invention arise from the following description in which these drawings are explained as well as invention is described.

BRIEF DESCRIPTION OF THE DRAWINGS

In the drawings,

FIG. 1 is an outside view of the probe tip of an optical probe according to the invention, FIG. 2 is a longitudinal section of such a probe tip, FIG. 3 is a cross section along line III—III of FIG. 1, FIG. 4 is a cross section of another sensor, FIG. 5 depicts a longitudinal section of a single sensor, FIG. 6 is a longitudinal section of a probe tip illustrating the feature of a stabilizing wire.

DETAILED DESCRIPTION OF THE INVENTION

Figure 7:
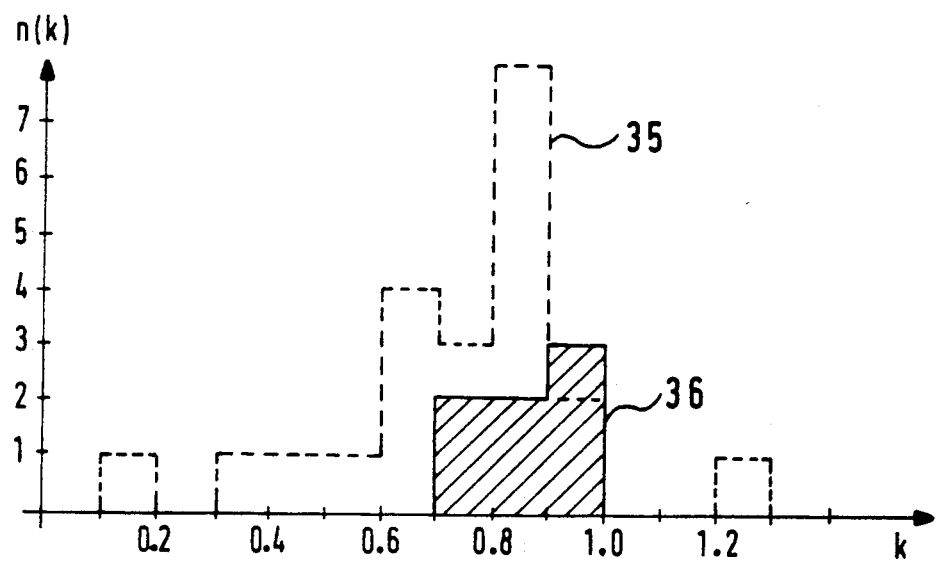
FIG. 7 depicts a diagram illustrating the effect of low temperature sterilization on sensor intensity for a pH sensor and FIG. 8 is a similar diagram relating to a $pCO_2$ sensor.

In FIG. 1, an optical probe is generally referred to as 1. FIG. 1 does not show the complete probe, but merely the probe tip.

A tubing element 2 surrounds a plurality of optical fibers. In FIG. 1, only one optical fiber 3 is shown (for graphical purposes). An envelope 4 surrounds this optical fiber.

Tubing element 2 is connected (as will be further explained in FIG. 2) with a sheath 5 which consists—in the shown example—of metal, preferably stainless steel. This sheath surrounds a plurality of sensors—two of which are shown in FIG. 1 and referred to as 6 and 7—, each of these sensors being an integral part together with the associated optical fiber.

For the details and the operation principle of such a sensor, reference is now made to FIG. 5 which shows the details of sensor 6 in longitudinal section. Light guided in optical fiber 3 reaches a dye-containing gel 8, the absorption spectrum of said dye—for example, phenol red—being dependent on the pH value of the blood. The light is then reflected at reflector 9. The whole system is packed in a selective membrane or envelope 10, this membrane being permeable for the ions or gas molecules to be measured—in case of a pH electrode, for hydrogen ions—, so that these ions/gas molecules can reach the dye-containing gel. Membrane 10 is fastened on the optical fiber 3 and the reflector 9 by a glue 11. The preferred material for membrane 10 is a hydrophilic material such as cellulose.

Therefore, light is directed into the optical fiber in the direction of arrow 12, passes the dye-containing gel 8—the absorption of which depends on the parameter to be measured—, is reflected at reflector 9 (this reflector is preferably made of metal such as platinum or stainless steel, the surface of this metal being polished on the side of gel 8), passes gel 8 again and is guided back through the optical fiber as indicated by arrow 13. A monitor measures the intensity of the reflected light to determine the parameter to be measured. Preferably, the light is transmitted and received in the form of a train of light pulses, but this is not a strict requirement. Optical fiber 3 is preferably a plastic fiber to ensure that it cannot break off inside a patient's artery; furthermore, a plastic fiber may be sterilized by gamma rays. To reduce cross interferences, the selective membranes should be selected according to the parameter to be measured; e.g., the membrane surrounding a $pCO_2$ sensor should not be permeable to hydrogen ions, but only for gas molecules. Gel 8 is used to immobilize the respective dye.

Returning now to FIG. 1, sheath 5 provides three openings to allow the blood to reach the diffusion zones (i.e. the region of the dye-containing gel) of the sensors. Two of these openings 14 and 15 are shown in FIG. 1. The outer end of sheath 5 is closed by a metal cap 16 (this metal cap is generated by welding or soldering and is further welded or soldered to sheath 5); after welding or soldering, projecting burrs are removed by electro-polishing to avoid injury of the patient's artery. Although indicated as 16', the connection line between metal cap 16 and sheath 5 is no longer visible after manufacturing.

The various sensors are fastened within sheath 5 by means of a silicone glue or adhesive 17. Placing and distribution of this glue will be explained by means of FIGS. 3 and 4.

FIG. 2 depicts a longitudinal section of the probe tip. In this section, details of the sensors (as just explained by means of FIG. 5) are shown. For example, the dye-containing gel of pH sensor 6 is outlined as 18, whereas its reflector is referred to as 19 and the semi-permeable envelope as 20. In similar manner, 21 is the optical fiber leading to a blood gas sensor 7 (for example, a $pO_2$ sensor), 22 is the dye-containing gel of this sensor, 23 its reflector and 24 its semi-permeable envelope (which should be permeable for gas molecules, but neither for water molecules nor for hydrogen ions in this case). FIG. 2 further depicts the third opening 25 in sheath 5. As shown by 26, tubing element 2 is introduced into sheath 5 and secured by adhesive means. Silicone glue 17 fills the space between the sensors and between the sensors and the sheath, respectively. $pO_2$ sensor 7 is completely embedded in this glue, whereas the outside 27 of pH sensor 6 is not covered by the glue although its rear side is in contact with said glue.

Openings 14, 15 and 25 of sheath 5 are manufactured by spark errosion. Upon manufacturing, it has to be ensured that no burrs or projecting edges are created in order to avoid any injury of the wall of the patient's artery.

The details of the manufacturing process will now be explained by means of FIG. 3 which is a cross section along line III—III of FIG. 1 in enlarged scale. Within sheath 5, pH sensor 6 and $pO_2$ sensor 7 and their appropriate reflectors 19 and 23 as well as their semi-permeable envelopes 20 and 24 are located. A further sensor 27 is used for $pCO_2$ measurement; its reflector is referred to as 28 and its semi-permeable envelope as 29. This sensor is not shown in FIG. 1 because it is hidden under sheath 5.

A wire 30 is used for strain relieving of the probe. Fastening of this sensor to metal cap 16 will be shown by means of FIG. 6.

Upon manufacturing of the probe, sheath 5 is placed in approximately horizontal position. Then, $pO_2$ sensor 7, $pCO_2$ sensor 27, pH sensor 6 and wire 30 are introduced into the sheath such that pH sensor 6 is on top of the other sensors and the wire.

In the next step, a silicone glue is introduced or injected into the interior of sheath 5, e.g. through one of openings 14, 15 and 25. The interior of sheath 5 is not completely filled with glue; instead, the upmost portion is left empty. Blood gas sensors 7 and 27 are completely embedded in the silicone glue. Gas molecules can diffuse through one of the openings 14, 15, 25 of sheath 5 and through semi-permeable envelopes 24 and 29 to reach the diffusion zones of sensors 7 and 27.

pH sensor 6 is not completely embedded in the silicone glue. Instead, only the lower portion of this sensor is kept in place by the glue. The upper portion of pH sensor 6 is not covered by glue, and the silicone glue also does not tend to creep upwards. Therefore, hydrogen ions may reach the semi-permeable envelope 20 and diffuse into the diffusion zones (i.e. the zone containing the gel). Therefore, the silicone glue does not impair the pH measurement.

On the other hand, the silicone glue is rather elastic. This ensures that the sensors can move in case of temperature changes. Further, the placement of the sensors within sheath 5 is not critical as at least the blood gas sensors (7 and 27) must not be placed directly adjacent to one of the openings of sheath 5 (as shown by way of $pCO_2$ sensor 27).

FIG. 4 depicts a similar cross section of another probe. It simply illustrates that a strain relieving wire is not absolutely mandatory for such a probe. In this case, all sensors are positioned adjacent to appropriate openings of sheath 5'. In this figure, the pH sensor is outlined as 6', the $pO_2$ sensor as 7' and the $pCO_2$ sensor as 27'. The silicone glue is referred to as 17'.

FIG. 6 depicts a longitudinal section of another probe tip 31 to illustrate the strain relieving means. Sheath 32 is closed at its outer end by metal cap 33. A strain relieving wire 34 is welded or soldered to said cap upon welding or soldering of metal cap 33 to sheath 32, i.e. there is only one welding or soldering manufacturing step. Sheath 32, metal cap 33 and wire 34 are made of the same material and can be regarded as a single component after manufacturing. At the end of the cable (not shown), the wire is fastened to a connector or to tubing 2. For graphical purposes, the sensors are not shown in the cross section according to FIG. 6.

Figure 8:
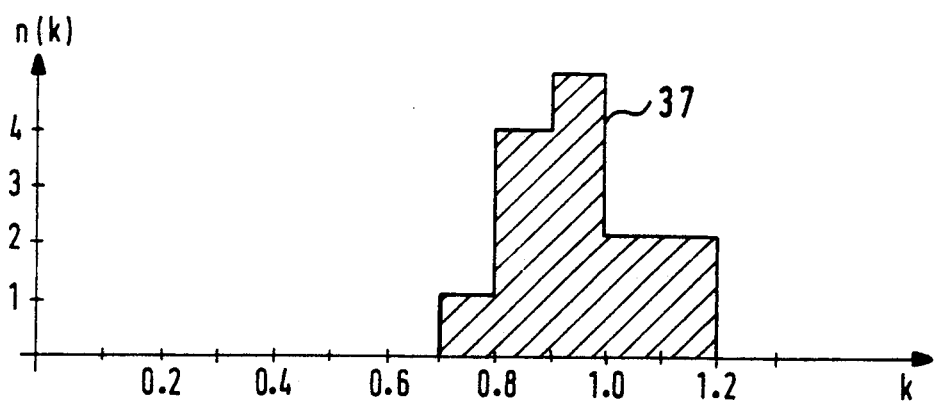

FIGS. 7 and 8 are used to illustrate the effect of sterilization at low temperatures on sensor intensity.

FIG. 7 relates to a pH sensor after cryogamma sterilization. The horizontal axis shows a relation k which is the proportion of sensor intensity after sterilization to the sensor intensity before sterilization, i.e.

$$k = \frac{\text{intensity after sterilization}}{\text{intensity before sterilization}}$$

The vertical axis shows the amount of sensors n (k) for a factor k' between k and k+0.1, i.e.

$$n(k') = \text{sensor count with } k' \in (k, k+0.1)$$

The test was carried out with 22 probes with fastening of the sensor inside the sheath by ordinary glue, in this case a PUR glue, and further with seven sensors using silicone glue. The obtained function n(k) for the case of PUR glue is depicted in a broken line and labeled as 35. The corresponding function for probes with silicone glue is labeled as 36 and hatched.

It is evident that the cryogamma sterilization has a considerably smaller effect on probes which are manufactured using silicone glue than on probes which are manufactured using ordinary glue. In particular, the average factor is $$\overline{k} = 0.74$$

in the case of probes with ordinary glue and $$\overline{k} = 0.87$$

in the case of probes with silicone glue.

A major reason for the better predictability of sensor intensity after cryogamma sterilization when using a silicone glue is that such a glue provides increased elasticity. As shown by way of FIG. 7, this is even true in the case of a pH sensor which is only partially covered by the silicone glue.

FIG. 8 shows a similar example of the function n (k) for a pCO₂ sensor. In this figure, only the function 37 for a silicone gluemanufactured probe is shown. A test with fourteen probes revealed a very impressing average value of $$\overline{k} = 0.96$$

I claim:

1. An optical probe comprising:
   an outer sheath having a first end, a second end, and at least one opening therethrough between said first end and said second end;
   a blood gas sensor unit positioned within said sheath comprising an optical fiber having a first end and a second end, said first end terminating within said sheath, said blood gas sensor unit further comprising a portion of gel positioned adjacent said first end of said optical fiber, said portion of gel having at least one dye therein, said dye having an absorption spectrum dependent on the concentration of a blood gas selected from the group consisting of oxygen and carbon dioxide, and a reflector unit positioned adjacent said portion of gel for reflecting light from said optical fiber which has passed through said portion of gel;
   a pH sensor unit positioned within said sheath comprising an optical fiber having a first end and a second end, said first end terminating within said sheath, said pH sensor unit further comprising a portion of gel positioned adjacent said first end of said optical fiber, said portion of gel having at least one dye therein, said dye having an absorption spectrum dependent on hydrogen ion concentration, and a reflector unit positioned adjacent said portion of gel for reflecting light from said optical fiber which has passed through said portion of gel; and
   a portion of gas-permeable adhesive within said sheath, said adhesive entirely covering said blood gas sensor unit, and covering only part of said pH sensor unit in order to divide said pH sensor unit into an uncovered section and a covered section, said uncovered section being positioned directly adjacent to and in alignment with said opening in said sheath in order to allow blood passing through said opening to come in contact with said uncovered section.

2. The probe of claim 1 wherein said adhesive comprises a silicone adhesive.

3. The proble of claim 1 wherein said sheath comprises a rigid cap member at said first end thereof, said probe further comprising a support wire within said sheath ajacent said pH sensor unit and said blood gas sensor unit, said support wire being secured to said cap member.

* * * * *